United States Patent
Gharib et al.

(10) Patent No.: US 7,715,018 B2
(45) Date of Patent: May 11, 2010

(54) 3-DIMENSIONAL IMAGING BY ACOUSTIC WARPING AND DEFOCUSING

(75) Inventors: Morteza Gharib, San Marino, CA (US); Joshua Adams, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 377 days.

(21) Appl. No.: 11/784,304

(22) Filed: Apr. 5, 2007

(65) Prior Publication Data

US 2007/0236694 A1    Oct. 11, 2007

Related U.S. Application Data

(60) Provisional application No. 60/789,335, filed on Apr. 5, 2006.

(51) Int. Cl.
*G01B 11/24* (2006.01)
(52) U.S. Cl. .................... 356/601; 356/614
(58) Field of Classification Search ......... 356/601–623, 356/394, 445; 382/154
See application file for complete search history.

(56) References Cited

U.S. PATENT DOCUMENTS 5,235,857 A    8/1993    Anderson
5,714,762 A *  2/1998    Li et al. .................... 250/559.2

FOREIGN PATENT DOCUMENTS

WO    WO 01/86281 A1    11/2001

* cited by examiner

*Primary Examiner*—Hoa Q Pham
(74) *Attorney, Agent, or Firm*—Law Ofc SC Harris (57) ABSTRACT

The present invention relates to a system for three-dimensional (3-D) acoustic imaging of a scattering structure using information from a two-dimensional (2-D) image. The system uses a characterized sensor array to emit a signal from the sensor array into an object of interest to generate at least one 2-D representation of the object of interest. The 2-D representation comprises a plurality of x and y coordinate pairs and at least one candidate scattering structure. The candidate scattering structure comprises a shape defined by at least one pair of x and y coordinates. The candidate scattering structure shape is restricted to at least one pair of x and y coordinates. The pair of x and y coordinates of the candidate scattering structure shape are then compared with a first coordinate-dependent response function to assign an x, y, and z position of a scattering structure in 3-D space.

19 Claims, 7 Drawing Sheets

3-DIMENSIONAL IMAGING BY ACOUSTIC WARPING AND DEFOCUSING

PRIORITY CLAIM

The present application is a non-provisional utility application, claiming benefit of priority of U.S. Provisional Patent Application No. 60/789,335, filed Apr. 5, 2006, titled "3-Dimensional Imaging by Acoustic Warping and Defocusing."

GOVERNMENT RIGHTS

The U.S. Government has certain rights in this invention pursuant to Grant No. CTS0421568, awarded by the National Science Foundation.

BACKGROUND OF THE INVENTION (1) Technical Field

The present invention relates to a system for determining three-dimension (3-D) positional information of a scattering structure embedded within a material that is outside the traditional focal region of a characterized acoustic impulse signal and, more particularly, to a process for producing the 3-D positional information, size, and material composition of a scattering structure by inspecting artifacts in the form of sidelobes and other sources of distortion via the use of a look-up table or comparison function.

(2) Background

Two-dimensional (2-D) imaging techniques may be used to determine the location of a material or scattering structure within another material with varying degrees of resolution and certainty. In standard 2-D imaging, only objects within the region of focus of a sensor array system become well-defined areas in an image slice. Objects outside the region of focus introduce blurred and warped artifacts. Thus, existing 2-D imaging systems do not provide sufficient imaging information with respect to objects in the extended region.

However, in many circumstances, it is desirable to obtain well-defined imaging information from the extended region. Therefore, a continuing need exists for a process that allows a user to gather acoustic imaging information of a scattering object contained within a known material quickly, using information from the extended region.

SUMMARY OF THE INVENTION

The present invention is a system for determining the position of a scattering structure in three-dimensional (3-D) space using information from a two-dimensional (2-D) image. Such a process is performed through using a characterized sensor array to emit a signal from the sensor array into an object of interest to generate at least one 2-D representation of the object of interest. The 2-D representation comprises a plurality of x and y coordinate pairs and at least one candidate scattering structure. The candidate scattering structure is a shape defined by at least one pair of x and y coordinates. The candidate scattering structure shape is substantially restricted to the at least one pair of x and y coordinates. The at least one pair of x and y coordinates of the candidate scattering structure shape are then compared with a first coordinate-dependent response function to assign an x, y, and z position of a scattering structure in 3-D space.

In another aspect, the system is further configured with a second coordinate-dependent response function, where the first coordinate response function includes characteristics representing a first scattering structure comprised of a first material and a second coordinate-dependent response function representing a second scattering structure representing a second material.

In yet another aspect, the system compares the at least one pair of x and y coordinates of the candidate scattering structure shape with a coordinate-dependent response function, at least one of the coordinate-dependent response functions further relates the candidate scattering structure view with the scattering structure size.

In another aspect, the system further compares the at least one pair of x and y coordinates of the candidate scattering structure shape with a first coordinate-dependent response function. The coordinate-dependent response function is a look-up table comprising a plurality of relationships relating the x and y coordinate pairs of a candidate scattering structure view with an x, y, and z position in 3-D space.

Additionally, when using a characterized sensor array, the signal of the characterized sensor array is an asymmetric signal.

In yet another aspect, the system is further configured to perform a scattering structure registration operation. The scattering structure registration is performed by using the characterized sensor array to emit a signal from the sensor array into a known material to capture at least one 2-D image of a scattering structure of known size in at least one location in 3-D space. The scattering structure resides substantially within the known material such that at least one image of the scattering structure of known size is outside the region of focus of the characterized sensor array. An image shape and the x, y, and z positional information of the scattering structure in 3-D space are recorded in a coordinate-dependent look-up table. The position of the characterized sensor array with respect to the known material is then adjusted. Additionally, a characterized sensor array is used again to emit a signal from the sensor array into a known material to capture at least one 2-D image of a scattering structure of known size in at least one location in 3-D space. As was the case above, the scattering structure resides substantially within the known material such that at least one image of the scattering structure of known size is within the region of focus of the characterized sensor array. Furthermore, an image shape and the x, y, and z positional information of the scattering structure in 3-D space are recorded in a coordinate-dependent look-up table.

Finally, the present invention also includes a method and computer program product. The method comprises a plurality of acts that embody the operations described herein. Additionally, the computer program product comprises computer-readable instruction means stored on a computer-readable medium that are executable by a computer for causing the computer to perform said operations.

BRIEF DESCRIPTION OF THE DRAWINGS

The objects, features and advantages of the present invention will be apparent from the following detailed descriptions of the disclosed aspects of the invention in conjunction with reference to the following drawings, where.

DETAILED DESCRIPTION

The present invention is an improved process for determining positional information in three dimensions of a scattering structure embedded within a material using acoustic imaging techniques. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 108, Paragraph 6. In particular, the use of "step of" or "act of" in the claims herein is not intended to invoke the provisions of 35 U.S.C. 108, Paragraph 6.

Before describing the invention in detail, a glossary of terms used in the description and claims is provided. Next, details of the present invention are provided to give an understanding of the specific aspects. Then, an overview of the principal aspects of the present invention is presented.

(1) Glossary

Before describing the specific details of the present invention, a glossary is provided in which various terms used herein and in the claims are defined. The glossary provided is intended to provide the reader with a general understanding of the intended meaning of the terms, but is not intended to convey the entire scope of each term. Rather, the glossary is intended to supplement the rest of the specification in more accurately explaining the terms used.

Asymmetric Signal—The term "asymmetric signal" refers to a signal which lacks symmetry in either the in x-y, y-z, or x-z planes. Generally, the asymmetric signal may be any signal which may be used to bias warping and defocusing in a candidate scattering structure.

Candidate Scattering Structure—The term "candidate scattering structure" refers to a shape in a two-dimensional (2-D) acoustic image defined by at least one pair of x and y coordinates which may or may not be associated with a scattering structure.

Characterized Sensor Array—The term "characterized sensor array" refers to a sensor array in which the strength and shape of the emitted signal from the sensor array has been measured in the x, y, and z dimensions. The parameters of the characterized sensor array may be established immediately following production of the sensor array, prior to searching for candidate scattering structures embedded within a material, or subsequent to searching for the candidate scattering structures. In general, it is desirable to characterize the sensor array prior to searching for candidate scattering structures in order to expedite the searching process.

Coordinate-Dependent Response Function—The term "coordinate-dependent response function" refers to a table or mathematical function relating information gathered from a scattering structure in response to a characterized sensor array signal where the distance between the scattering structure and characterized sensor array has been varied.

Instruction Means—The term "instruction means" as used with respect to this invention generally indicates a set of operations to be performed on a computer, and may represent pieces of a whole program or individual, separable, software modules. Non-limiting examples of "instruction means" include computer program code (source or object code) and "hard-coded" electronics (i.e., computer operations coded into a computer chip). The "instruction means" may be stored in the memory of a computer or on a computer-readable medium such as a floppy disk, a CD-ROM, and a flash drive.

Sensor Array—The term "sensor array" is used to describe any system of cooperative signal emitters and signal receivers used to gather response information from both in focus and out of focus scattering structures. Non-limiting examples of suitable sensor arrays include standard sonic imaging systems such as a one dimension (1-D) linear array of sensing elements, one and one-half dimension (1.5-D) phased arrays, two dimension (2-D) arrays, and, in general, arbitrary 3-D distributions of transmitting and sensing elements.

(2) Specific Details of the Invention

Figure 1:
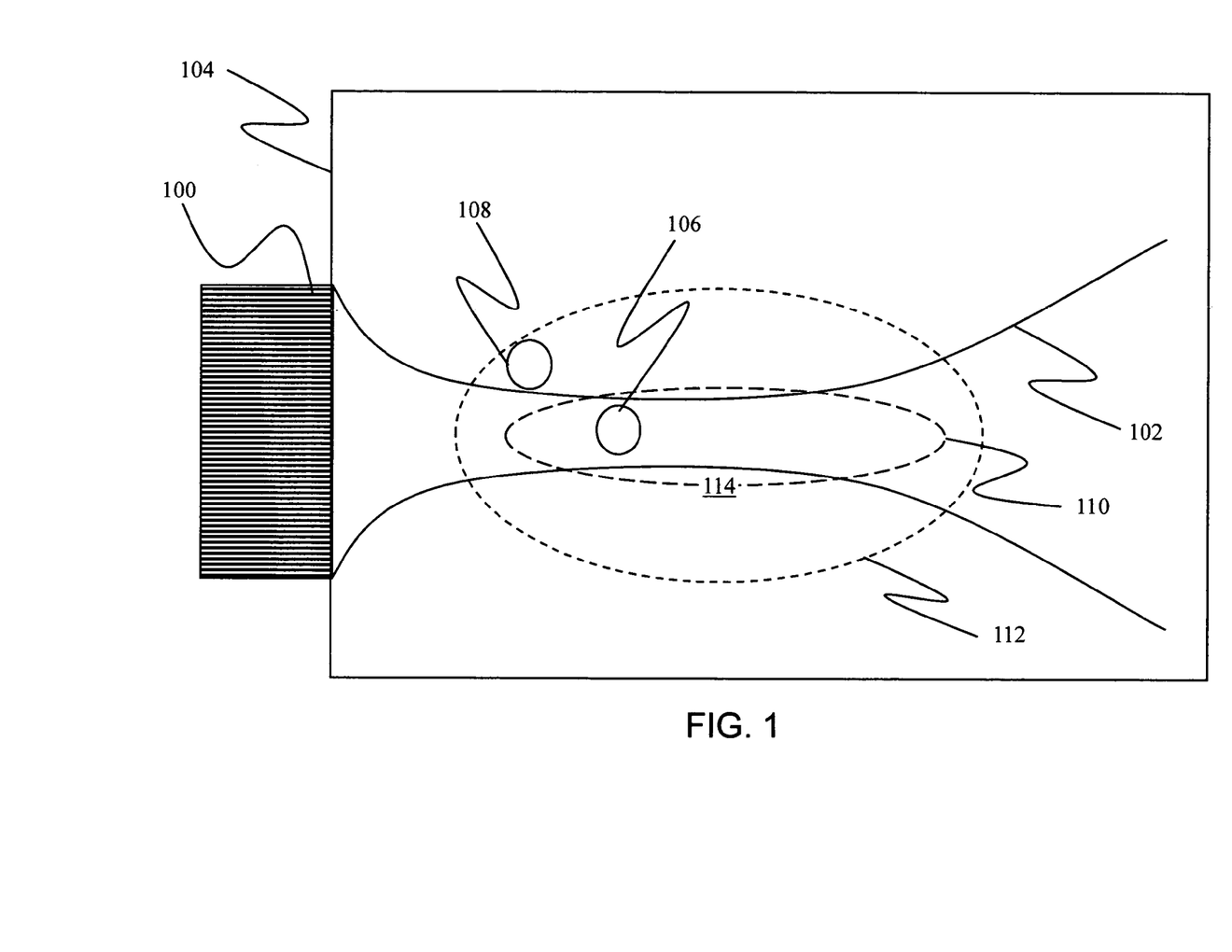
FIG. 1 is an illustration contrasting an in-focus area from which conventional two-dimensional (2-D) imaging techniques may extract information from a scattering structure and that area from which useful information may be extracted from out-of-focus scattering structures.

As mentioned above, the present invention relates to an acoustic imaging technique for determining three-dimensional positional information regarding a scattering structure embedded within a material. As shown in FIG. 1, an array of sensors 100 can be configured to emit a signal 102 into an object of interest 104 and in return receive a response signal as the signal 102 propagates through the material 104 back towards the sensor array 100. The array of sensors 100 is any suitable sensor array that is capable of emitting and receiving a signal, a non-limiting example of which includes an array of piezoelectric transducers. In operation, scattering structures 106 within the material 104 oscillate back and forth in response to the signal 102. In general, a scattering structure 106, will respond to an emitted signal 102 with a characteristic response related to the size and material composition of the scattering structure 106, the distance between the scattering structure 106 and the sensor array 100, and the emission pattern of the sensor array 100. The vibrations of the scattering structures 106 are picked up by the sensor array 100 as the vibrations are transferred through the material 104. Although the signal 102 from the sensor array 100 is essentially limited to two planes, for example the x and z plane, a scattering structure 108 outside the focal region 110 of the sensor array 100 will begin to oscillate in response to a scattering structure 106 within the focal region 110. The oscillations of these out-of-focus scattering structures 108 make a small contribution to the signal received by the sensor array 100, which often appear as obscured candidate scattering structure images 214 in the 2-D representations 204, shown in FIG. 2A.

Figure 2A:
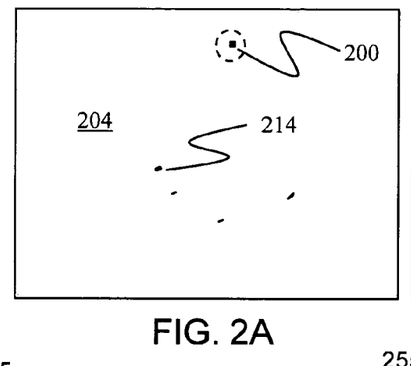
FIG. 2A is a 2-D image of an in-focus scattering structure response to a sensor array signal.

As shown in FIG. 2A, the oscillations within the focal region 110 produce the clearest 2-D representations 204 of potential candidate scattering structures 200. These 2-D images 204 of the candidate scattering structures 200, when combined with an asymmetric signal, can be used to detect additional information in a third dimension to produce a well-defined image slice 202, such as the one shown in FIG. 2B.

Figure 2B:
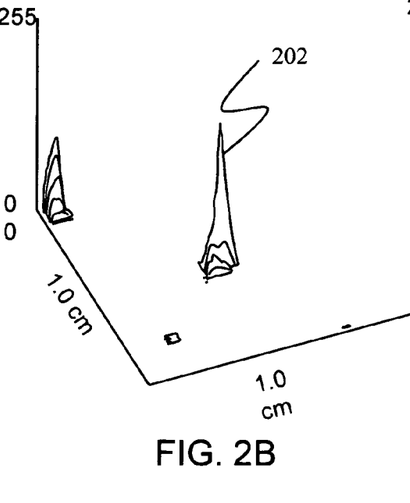
FIG. 2B is a three-dimensional (3-D) graph illustrating a well-defined, coordinate-dependent response to a characterized sensor array signal source.

When all distances are held constant except for the linear distance between the sensor array 100 and scattering structure 106, the linear distance between the sensor array 100 and scattering structure 106 is increased. Thus, the 2-D representation 206 of the candidate scattering structure 106 becomes less well-defined producing blurred and warped artifacts 200', shown in FIG. 2C. As a result, the sharpness of the image slice 208, shown in FIG. 2D, is also diminished. This trend continues as exemplified in FIG. 2E and FIG. 2F. In general, as a candidate scattering structure 200" is further removed from the focal region 110, the obscured 2-D representation 210 produces image slices 212 with more pronounced sub-blurred and warped artifacts 214 and 216. A registration process for a scattering structure 106 in a known material 104 may be conducted by capturing images 204, 206, and 210 with a characterized and asymmetric signal 102.

Specifically, referring to FIG. 1, the registration process characterizes a sensor array signal 102 and its point spread function into a warping map, which, like a fingerprint, is unique to the geometry and materials 104 comprising that array. This process involves recording the image of a scattering structure 106 with a known size at a number of positions within the entire field of view 114 of the sensing array 100, which includes both the focused region 110 and defocused region 112.

This information is then loaded into a look-up table and a mathematical de-convolution is performed with a standard image to extract scattering structure locations above 400 and 400' and below 406 and 406' the focal region 412 (see FIG. 4). The scattering structures appear as blurred or warped regions, and not sharp particles in captured 2-D images. With increasing z-distance, the point spread function tends to become more diffuse. The registration process takes this spread into account to calculate a more precise location of the scattering structure, despite the spread in pixels.

The incorporation of the registration process and de-warping and defocusing system into contemporary visualization methodologies can help to better locate objects out-of-plane. As can be appreciated by one skilled in the art, such a process is useful in a variety of fields, examples of which include acoustic surface and volume imaging of objects, particle image velocimetry (PIV), particle tracking velocimetry (PTV), Doppler tracking, and any other technique that seeks the locations of objects within a viewable region.

This system allows more particles to be found with an extra dimension of information. Referring again to FIG. 1, the present invention determines 3-D position information of acoustic scattering structures 106 inside the focal region 110 and scattering structures 108 in the area 112 outside the boundaries of the focal region 110 of the sensor array 100 acoustic signal 102 (such as in standard 2-D-slice ultrasound). Following a sensor array registration process, images (see FIGS. 2A, 2C, and 2E) produced through standard acoustic reflection techniques may be analyzed for out-of-focus data 200' and 200" present in the form of warped or blurred artifacts.

Figure 2C:
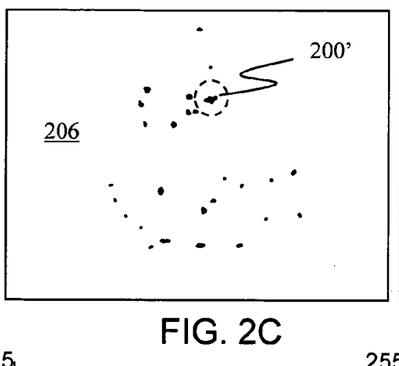
FIG. 2C is an image of an out-of-focus candidate scattering structure response to a somewhat distant-characterized sensor array signal source.
Figure 2D:
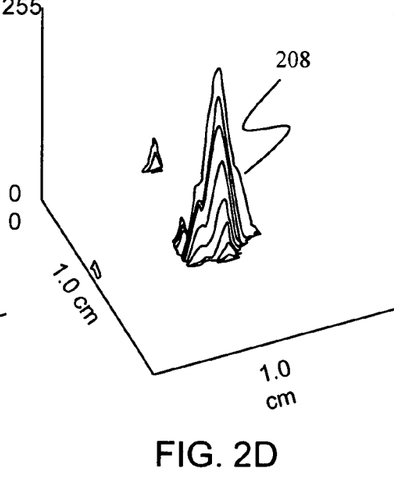
FIG. 2D is a 3-D graph illustrating a coordinate-dependent response to a somewhat distant-characterized sensor array signal source.
Figure 2E:
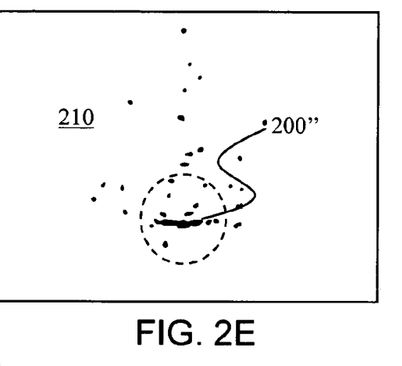
FIG. 2E is a 2-D image of an out-of-focus scattering structure response to a distant sensor array.
Figure 2F:
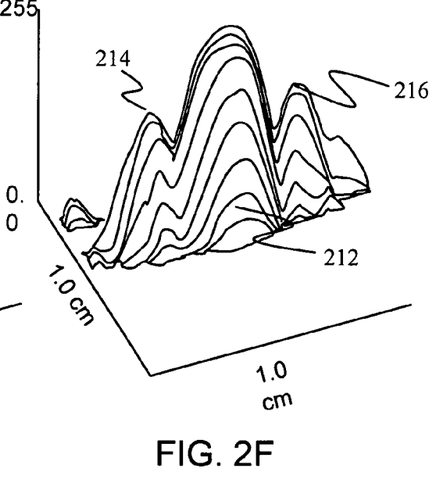
FIG. 2F is a 3-D graph illustrating a poorly defined coordinate-dependent response function in which the characterized sensor array signal source is a great distance away from the candidate scattering structure.

FIGS. 2A, 2C and 2E illustrate a sequence of 2-D ultrasound images of a reflector whose position changes in each frame. The probe is centered at the top of each image. Alternatively, FIGS. 2B, 2D, and 2F illustrate the corresponding 3-D representations. In FIGS. 2A and 2B, the scattering structure is near the probe, which produces a well-defined (sharp) image slice. As the scattering structure is moved away from the probe (as reflected in FIGS. 2C through 2F), the image slice loses definition (sharpness). This changing profile, or point spread function, changes with position in x, y, and z. While these images show the changes within the x-z plane, the registration process also performs characterization in the y-direction (which is into and out of the page) to characterize the sonic array for de-warping in 3-D for particle locating.

Scattering structures appear different in the image depending on where in the field of view they are located (see FIGS. 2A, 2C, and 2E). With increasing z-distance, the point spread function (see FIGS. 2B, 2D, and 2F) tends to become more diffuse. The registration process takes this spread into account to calculate a more precise location of the scattering structure, despite the spread in pixels.

Although not limited thereto, the present invention utilizes acoustic and other qualitative positional analysis to identify the x-y-z position in a "right-handed coordinate system" of out-of-focus 108 and out-of-plane reflectors.

Figure 3:
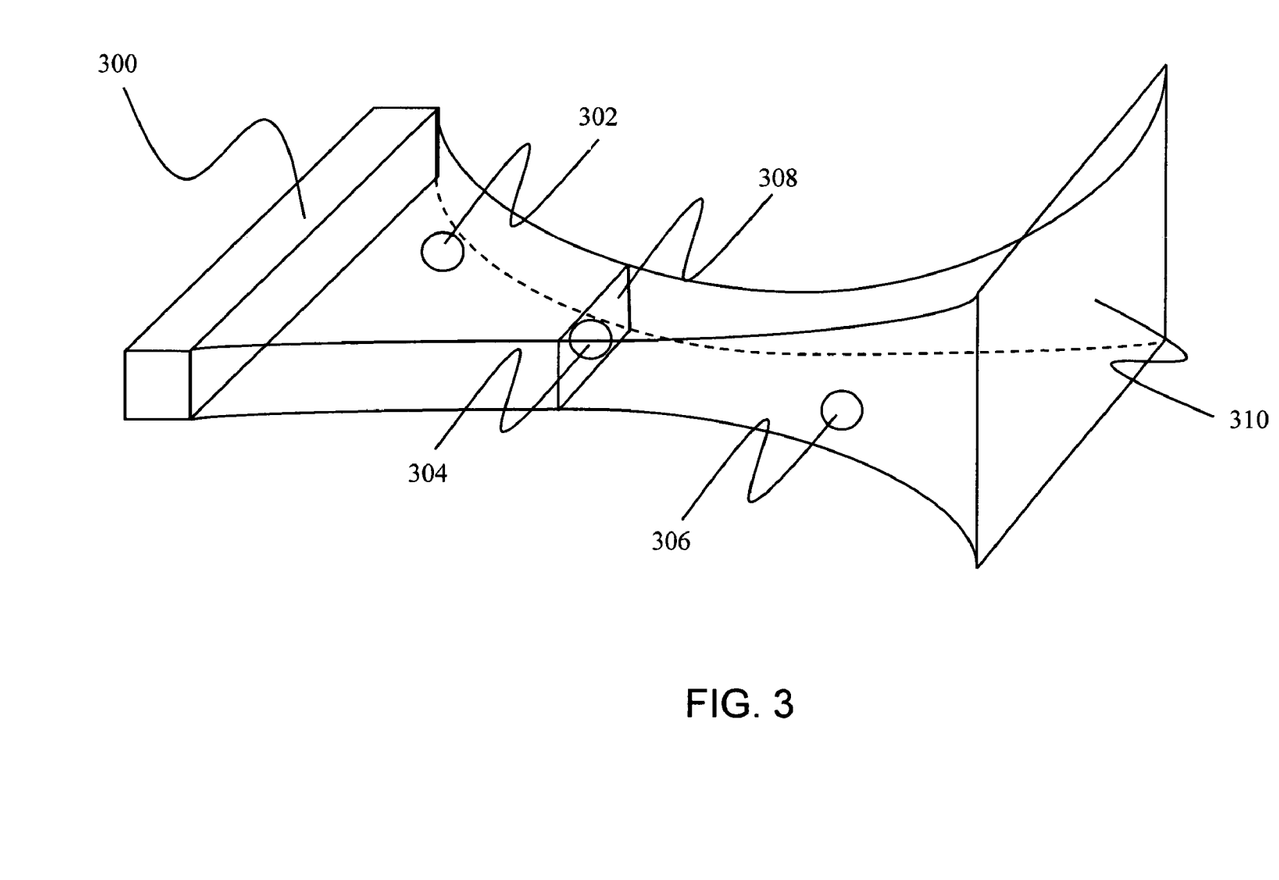
FIG. 3 is an illustration of a sensor array and characterized sensor array signal used to detect both in-focus and out-of-focus scattering structures.

Referring to FIG. 3, the asymmetric properties of the signal 310 enable reflected signals from out-of-beam scattering structures 302 and out-of-focus scattering structures 306 to contribute discernable positional information with regard to their x-y-z position. By varying the distance between the sensor array 300 and a particular scattering structure of known size at known distances, the collected scattering structure information can be used to develop a coordinate-dependent response look-up table or response function. A perspective view of scattering structures 302, 304, and 306 demonstrates possible scattering positions during the registration process. FIG. 3 illustrates the spatial relationship between the sensor array 300, an emitted characterized signal 310, a close-proximity scattering structure 302, an in-focus scattering structure 304, and an out-of-focus in-signal scattering structure 306. The asymmetric signal 310 has an in-focus area 308, which is by definition the narrowest portion of the signal. A scattering structure 306 within the in-focus area 308 will typically produce a clean 2-D images 200, as shown in FIG. 2A. By moving the scattering structure into close-proximity, in-focus, and out-of-focus positions (represented by scattering structures 302, 304, and 306, respectively) over a series of pulses, repeated multiple times, a series of 2-D images can be iteratively produced. The 2-D images are used to develop the coordinate-dependent response look-up table. The scattering structure 302, 304, and 306 will respond with a distribution based on the shape of the originating signal pattern 310. By utilizing data based on the signal pattern 310, out-of-focus in signal scattering structures 306 can be inferred to have a height in the y-direction, which is generally not available data in 2-D imaging. Further, above scattering structures 302 versus below scattering structures 308 are distinguished by actively imparting asymmetry into the beam pattern so that the beam profile is identifiable top or bottom.

Figure 4:
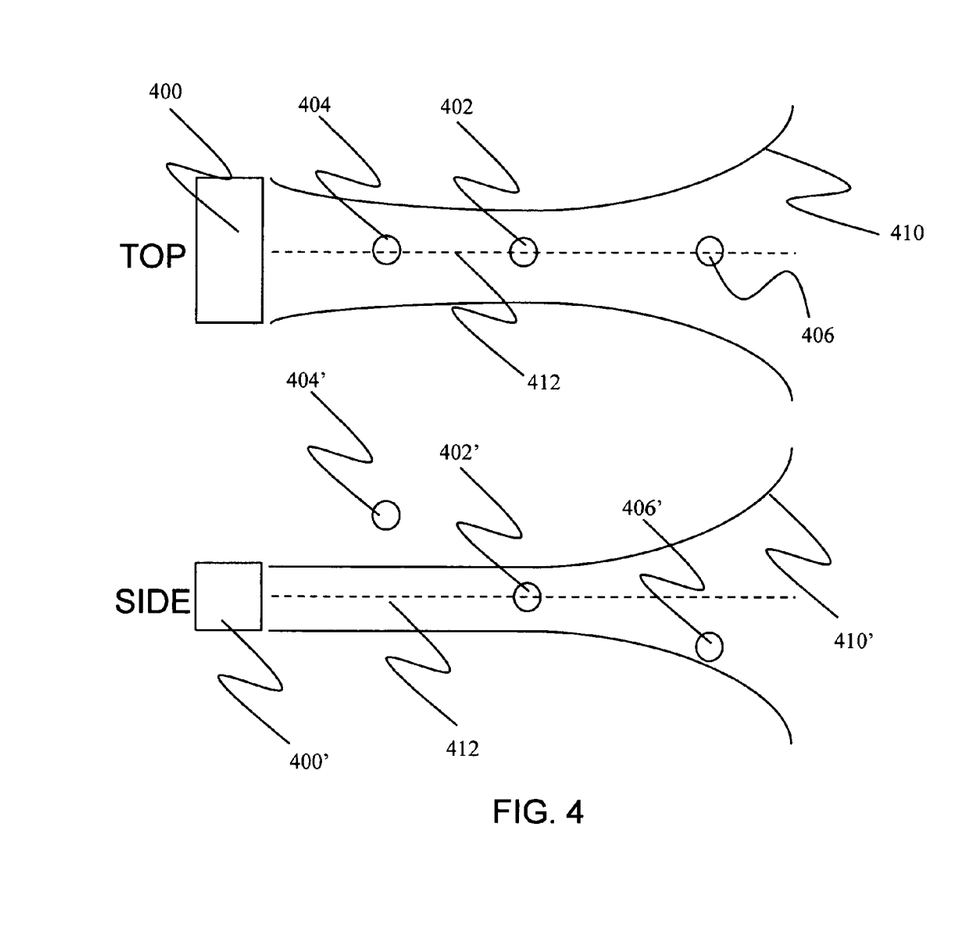
FIG. 4 is an illustration of both a top-view and side-view of a sensor array and characterized sensor array signal that is used to detect both in-focus and out-of-focus scattering structures.

Additionally, FIG. 4 illustrates three acoustic reflectors, 402, 404, and 406, each having the same x-coordinate, but at varying distance, z, from the sensor array. The three reflectors 402, 404, and 406 are also at positions that vary in y, above and below the image plane (x-z). Reflector 402 is within the focal plane at the optimum location for 2-D imaging which would show up as a sharply defined reflector in a standard image. Reflector 406 is beyond the optimum focal distance. Thus, reflector 406 appears as a much larger structure (in number of pixels) that is not sharply defined and generally weaker in overall response brightness. The present invention determines a more precise distance in z, as well as distance from an x-y image plane in y based on a comparison with the look up table. Alternatively, reflector 404 is in the nearfield and substantially above the imaging plane. Some energy is transmitted and received from a reflector in such a position. In standard imaging, such a response is typically not seen by visual inspection due to the energy being spread over many or all of the pixels in the obtained 2-D image. However, the present invention finds such reflectors by matching large diffuse regions of the 2-D image with the look-up table. The look-up tables can also be referred to as warping maps, each of which may be created for a different material through the registration process.

Controlling the focal distance in phase arrays allows for scattering structure characterization. Signal forming and warping may be used to form an asymmetric signal 510 such as the one shown in FIG. 5. The asymmetric signal 510 may be created to code an upper half plane, the area above the nominal signal plane 508, as well as a bottom half plane, the area below the nominal signal plane 508. For example, as a signal 510 encounters a scattering structure 512 residing either above or below the nominal signal plane 508, the asymmetry of the signal 510 is able to reflect back to the sensor 500 a coordinate-dependent response function that will reveal the plane in which the structure 512 resides.

Figure 5:
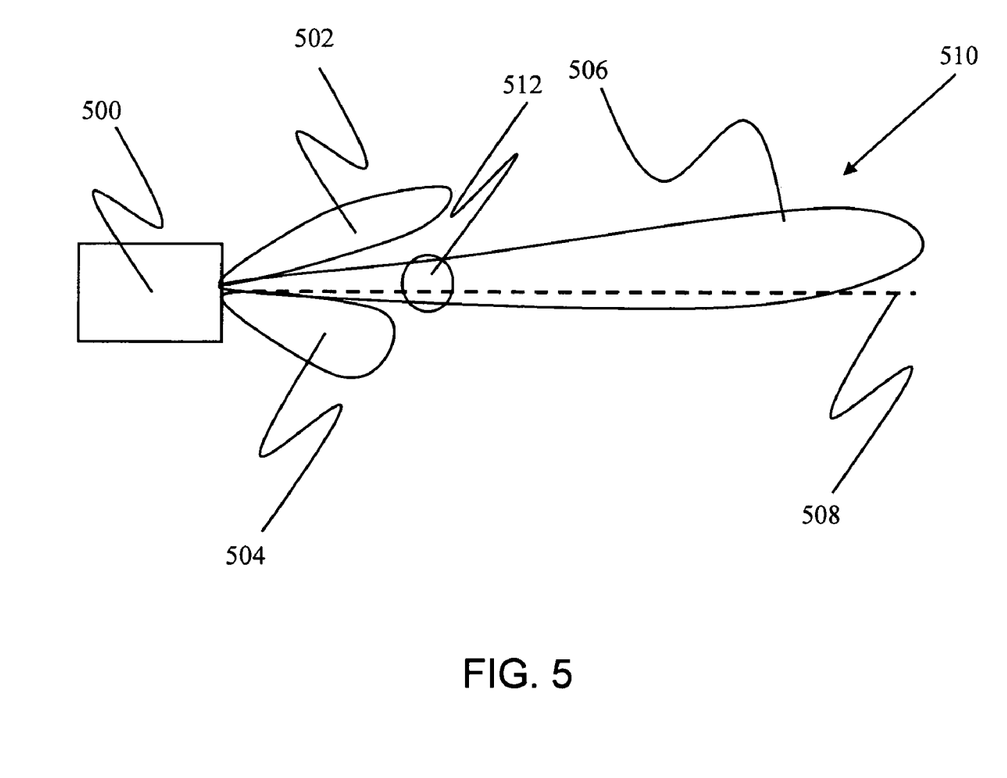
FIG. 5 is an illustration of a signal forming to create asymmetry in the x-y, y-z, or x-z planes to bias warping and defocusing in the scattering structures or object acoustic.

FIG. 5 illustrates a possible signal forming shape 510 that includes an upper lobe 502, a center lobe 506, and a bottom lobe 504 to create asymmetry in x-y, y-z or x-z planes to bias warping and defocusing in the scattering structure 512. Possible methods for signal forming include, but are not limited to, phase array distortion, acoustic lenses, and spatial-complete or partial-path blockage.

(3) Principal Aspects

The present invention has three "principal" aspects. As described above, the first is a system for 3-D imaging using acoustic warping and defocusing. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

Figure 6:
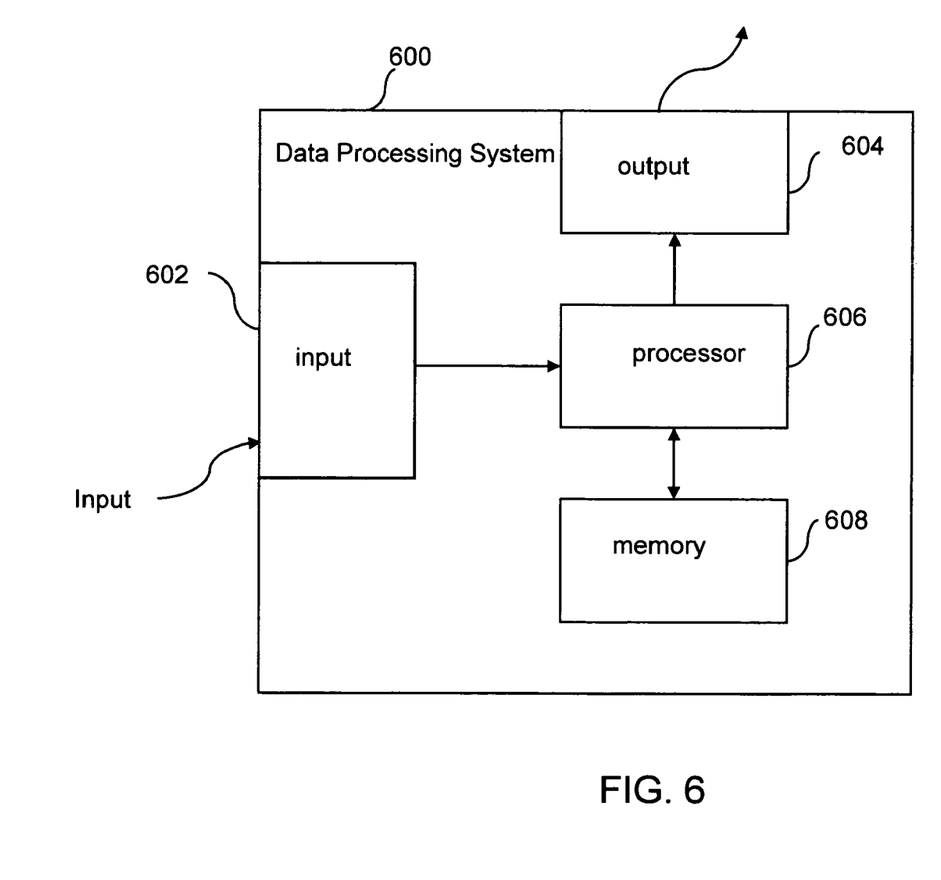
FIG. 6 is a block diagram of a 3-D imaging system according to the present invention.

A block diagram depicting the components of a 3-D imaging system of the present invention is provided in FIG. 6. The image processing system 600 comprises an input 602 for receiving information from at least one sensor (e.g., transducer array) for use in detecting an image. Note that the input 602 may include multiple "ports." Typically, input is received from at least one sensor, non-limiting examples of which include video image sensors. An output 604 is connected with the processor for providing information regarding the presence and/or identity of object(s) in the scene to other systems in order that a network of computer systems may serve as an imaging system. Output may also be provided to other devices or other programs; e.g., to other software modules, for use therein. The input 602 and the output 604 are both coupled with a processor 606, which may be a general-purpose computer processor or a specialized processor designed specifically for use with the present invention. The processor 606 is coupled with a memory 608 to permit storage of data and software that are to be manipulated by commands to the processor 606.

Figure 7:
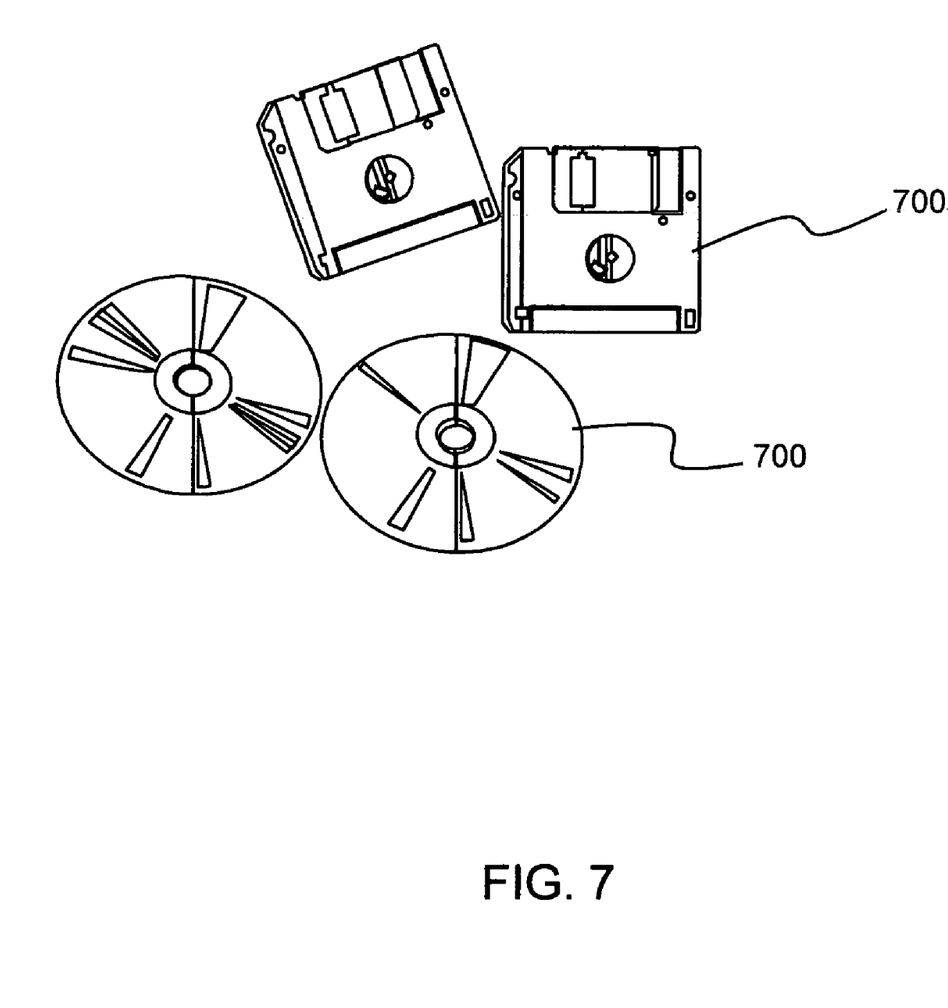
FIG. 7 is illustrative diagram of a computer program product embodying the present invention.

An illustrative diagram of a computer program product embodying the present invention is depicted in FIG. 7. The computer program product 700 is depicted as an optical disk such as a CD or DVD. However, as mentioned previously, the computer program product generally represents computer-readable instructions stored on any compatible computer-readable medium.

What is claimed is:

1. A method for determining the position of a scattering structure in three-dimensional (3-D) space using information from a two-dimensional (2-D) image, the method comprising acts of:

using a characterized sensor array to emit a signal from the sensor array into an object of interest to generate at least one 2-D representation of the object of interest, the 2-D representation comprising a plurality of x and y coordinate pairs and at least one candidate scattering structure, the candidate scattering structure comprising a shape defined by pairs of x and y coordinates; and comparing the pairs of x and y coordinates of the candidate scattering structure shape with a first coordinate-dependent response function to assign an x, y, and z position of a scattering structure in 3-D space.

2. A method as set forth in claim 1, further comprising an act of using a second coordinate-dependent response function, where the first coordinate response function includes characteristics representing a first scattering structure comprised of a first material and the second coordinate-dependent response function represents a second scattering structure representing a second material.

3. A method as set forth in claim 2, wherein in the act of comparing the pairs of x and y coordinates of the candidate scattering structure shape with a coordinate-dependent response function, at least one of the coordinate-dependent response functions further relates the pairs of x and y coordinates with a scattering structure size.

4. A method set forth in claim 1, wherein in the act of comparing the pairs of x and y coordinates of the candidate scattering structure shape with a first coordinate-dependent response function, the coordinate-dependent response function is a look-up table comprising a plurality of relationships relating the x and y coordinate pairs of a candidate scattering structure with an x, y, and z position in 3-D space.

5. A method as set forth in claim 1, wherein in the act of using a characterized sensor array, the signal of the characterized sensor array is an asymmetric signal.

6. A method as set forth in claim 1, wherein the method further comprises a scattering structure registration process, the scattering structure registration process comprising the acts of:
using the characterized sensor array to emit a signal from the sensor array into a known material to capture at least one 2-D first image shape of a scattering structure of known size in at least one location in 3-D space having a first x, y, and z positional information, wherein the scattering structure resides substantially within the known material such that an at least one image of the scattering structure of known size is outside the region of focus of the characterized sensor array;
recording the first image shape and the first x, y, and z positional information of the scattering structure in 3-D space in a coordinate-dependent look-up table;
adjusting the position of the characterized sensor array with respect to the known material;
using a characterized sensor array to emit a signal from the sensor array into a known material to capture at least one 2-D second image shape of a scattering structure of known size in at least one location in 3-D space having a second x, y, and z positional information, wherein the scattering structure resides substantially within the known material such that an at least one image of the scattering structure of known size is within the region of focus of the characterized sensor array; and
recording the second image shape and the second x, y, and z positional information of the scattering structure in 3-D space in a coordinate-dependent look-up table.

7. A system for determining the position of a scattering structure in three-dimensional 3-D space using information from a two-dimensional (2-D) image, the system being configured to perform operations of:
using a characterized sensor array to emit a signal from the sensor array into an object of interest to generate at least one 2-D representation of the object of interest, the 2-D representation comprising an array to emit a signal from the sensor array into an object of interest to generate at least a plurality of x and y coordinate pairs and at least one candidate scattering structure, the candidate scattering structure comprising a shape defined by pairs of x and y coordinates; and
comparing the pairs of x and y coordinates of the candidate scattering structure shape with a first coordinate-dependent response function to assign an x, y, and z position of a scattering structure in 3-D space.

8. A system as set forth in claim 7, wherein the system is further configured with a second coordinate-dependent response function, where the first coordinate response function includes characteristics representing a first scattering structure comprised of a first material and a second coordinate-dependent response function representing a second scattering structure representing a second material.

9. A system as set forth in claim 8, wherein the system compares the pairs of x and y coordinates of the candidate scattering structure shape with a coordinate-dependent response function, at least one of the coordinate-dependent response functions further relates the pairs of x and y coordinates with a scattering structure size.

10. A system as set forth in claim 7, wherein the system further compares the pairs of x and y coordinates of the candidate scattering structure shape with a first coordinate-dependent response function, the coordinate-dependent response function is a look-up table comprising a plurality of relationships relating the x and y coordinate pairs of a candidate scattering structure view with an x, y, and z position in 3-D space.

11. A system as set forth in claim 7, wherein when the act of using a characterized sensor array, the signal of the characterized sensor array is an asymmetric signal.

12. A system as set forth in claim 7, wherein the system is further configured to perform a scattering structure registration operation, the scattering structure registration operation comprising the operations of:
using the characterized sensor array to emit a signal from the sensor array into a known material to capture at least one 2-D first image shape of a scattering structure of known size in at least one location in 3-D space having a first x, y, and z positional information, wherein the scattering structure resides substantially within the known material such that an at least one image of the scattering structure of known size is outside the region of focus of the characterized sensor array;
recording the first image shape and the first x, y, and z positional information of the scattering structure in 3-D space in a coordinate-dependent look-up table;
adjusting the position of the characterized sensor array with respect to the known material;
using a characterized sensor array to emit a signal from the sensor array into a known material to capture at least one 2-D second image shape of a scattering structure of known size in at least one location in 3-D space having a first x, y, and z positional information, wherein the scattering structure resides substantially within the known material such that an at least one image of the scattering structure of known size is within the region of focus of the characterized sensor array; and
recording the second image shape and the second x, y, and z positional information of the scattering structure in 3-D space in a coordinate-dependent look-up table.

13. A computer program product for determining the position of a scattering structure in three-dimensional (3-D) space using information from a two-dimensional (2-D) image, the computer program product comprising computer-readable instruction means stored on a computer-readable medium that are executable by a computer for causing the computer to:
use a characterized sensor array to emit a signal from the sensor array into an object of interest to generate at least one 2-D representation of the object of interest, the 2-D representation comprising a plurality of x and y coordinate pairs and at least one candidate scattering structure, the candidate scattering structure comprising a shape defined by pairs of x and y coordinates; and
compare the pairs of x and y coordinates of the candidate scattering structure shape with a first coordinate-dependent response function to assign an x, y, and z position of a scattering structure in 3-D space.

14. A computer program product as set forth in claim 13, wherein the computer program product further comprises instruction means for causing a computer to use a second coordinate-dependent response function, where the first coordinate response function includes characteristics representing a first scattering structure comprised of a first material and a second coordinate-dependent response function representing a second scattering structure representing a second material.

15. A computer program product as set forth in claim 14, wherein the computer program product further comprises instruction means for causing a computer to perform the act of comparing the pairs of x and y coordinates of the candidate scattering structure shape with a coordinate-dependent response function, at least one of the coordinate-dependent response functions further relates the pairs of x and y coordinates with a scattering structure size.

16. A computer program product as set forth in claim 13, wherein the computer program product further comprises instruction means for causing a computer to compare the pairs of x and y coordinates of the candidate scattering structure shape with a first coordinate-dependent response function, the coordinate-dependent response function is a look-up table comprising a plurality of relationships relating the x and y coordinate pairs of a candidate scattering structure view with an x, y, and z position in 3-D space.

17. A computer program product as set forth in claim 13, wherein the computer program product further comprises instruction means for causing a computer to use a characterized sensor array where the emitted signal of the characterized sensor array is an asymmetric signal.

18. A computer program product as set forth in claim 13, wherein the computer program product further comprises instruction means for causing a computer to perform a scattering structure registration process, the scattering structure registration process comprising computer-readable instruction means stored on a computer-readable medium that are executable by a computer for causing the computer to:
  use the characterized sensor array to emit a signal from the sensor array into a known material to capture at least one 2-D first image shape of a scattering structure of known size in at least one location in 3-D space having a first x, y, and z positional information, wherein the scattering structure resides substantially within the known material such that an at least one image of the scattering structure of known size is outside the region of focus of the characterized sensor array;
  record the first image shape and the first x, y, and z positional information of the scattering structure in 3-D space in a coordinate-dependent look-up table;
  adjust the position of the characterized sensor array with respect to the known material;
  use a characterized sensor array to emit a signal from the sensor array into a known material to capture at least one 2-D second image shape of a scattering structure of known size in at least one location in 3-D space having a second x, y, and z positional information, wherein the scattering structure resides substantially within the known material such that an at least one image of the scattering structure of known size is within the region of focus of the characterized sensor array; and
  record the second image shape and the second x, y, and z positional information of the scattering structure in 3-D space in a coordinate-dependent look-up table.

19. A computer program product as set forth in claim 13, wherein the computer program product further comprises instruction means for causing a computer to:
  compare the pairs of x and y coordinates of the candidate scattering structure shape with a first coordinate-dependent response function, the coordinate-dependent response function is a look-up table comprising a plurality of relationships relating the x and y coordinate pairs of a candidate scattering structure view with an x, y, and z position in 3-D space; and
  use a characterized sensor array where the emitted signal of the characterized sensor array is an asymmetric signal.

* * * * *